United States Patent [19]

Seeberg-Elverfeldt

[11] Patent Number: 4,960,113
[45] Date of Patent: Oct. 2, 1990

[54] ERECTION AID

[76] Inventor: Herbert Seeberg-Elverfeldt, Curtiusstrasse 22, D-4006 Erkrath 2, Fed. Rep. of Germany

[21] Appl. No.: 299,641

[22] Filed: Jan. 23, 1989

Related U.S. Application Data

[63] Continuation-in-part of Ser. No. 47,489, May 11, 1987, abandoned.

[30] Foreign Application Priority Data

May 21, 1986 [DE] Fed. Rep. of Germany ....... 3617027

[51] Int. Cl.$^5$ ............................................. A61F 5/41
[52] U.S. Cl. .................................................. 128/79
[58] Field of Search ......................... 128/79, DIG. 25; 606/202

[56] References Cited

U.S. PATENT DOCUMENTS

| D. 258,690 | 3/1981 | Wu | D24/99 |
|---|---|---|---|
| 594,815 | 11/1897 | Taggart | 128/79 |
| 1,225,341 | 5/1917 | Lederer | 128/79 |
| 2,571,461 | 10/1951 | Livingston et al. | 128/327 |
| 2,874,698 | 2/1959 | Sell | 128/79 |
| 3,455,301 | 7/1969 | Clark | 128/79 |
| 3,495,589 | 2/1970 | Clement | 128/79 |
| 3,744,486 | 7/1973 | Wilson | 128/79 |
| 3,820,533 | 6/1974 | Jones | 128/79 |
| 4,139,007 | 2/1979 | Diamond | 128/79 |
| 4,175,554 | 11/1979 | Gerow | 128/79 |
| 4,378,008 | 3/1983 | Osbon, Sr. | 128/79 |
| 4,417,567 | 11/1983 | Trick | 128/DIG. 25 |
| 4,641,638 | 2/1987 | Perry | 128/79 |
| 4,723,538 | 2/1988 | Stewart | 128/79 |

FOREIGN PATENT DOCUMENTS

| 148586 | 7/1985 | European Pat. Off. | 128/79 |
|---|---|---|---|
| 427488 | 3/1926 | Fed. Rep. of Germany . | |
| 476413 | 5/1929 | Fed. Rep. of Germany | 128/79 |
| 565238 | 4/1931 | Fed. Rep. of Germany | 128/79 |
| 923695 | 2/1955 | Fed. Rep. of Germany | 128/79 |
| 7822298 | 1/1979 | Fed. Rep. of Germany | 128/79 |
| 347300 | 8/1960 | Italy . | |
| 154651 | 10/1932 | Switzerland . | |
| 21538 | of 1913 | United Kingdom | 128/79 |
| 1497441 | 1/1978 | United Kingdom | 128/79 |

Primary Examiner—Cary E. Stone
Attorney, Agent, or Firm—Walter C. Farley

[57] ABSTRACT

An erection aid comprises an annnular elastic tube which is inflatable to apply pressure to the base of the penis, reducing venous flow of blood while permitting arterial flow. A valve is provided for inflation. The annular tube is made with non-uniform wall thickness so that the inwardly facing portions of the wall are thinner and more easily deformable, permitting the desired pressure to be applied while minimizing axial deformation and thereby minimizing interference with normal functions. The thicker portions of the tube are sufficiently elastic to allow diametral increases as the penis becomes erect.

1 Claim, 3 Drawing Sheets

FIG. 2
FIG. 3
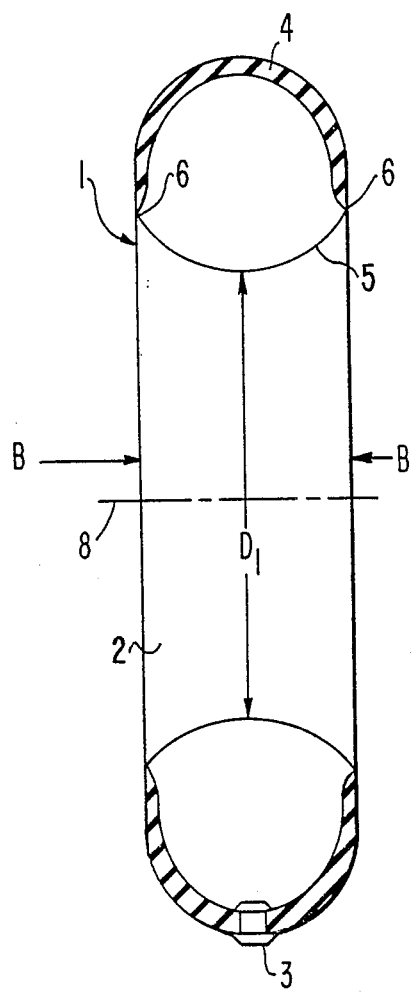
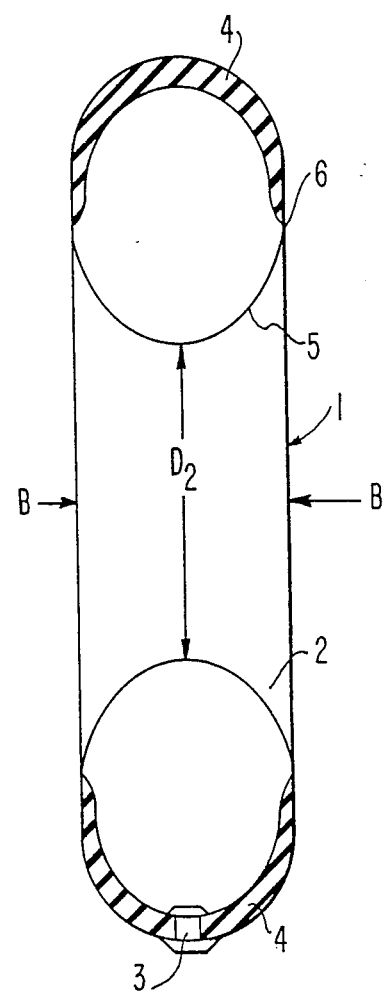

ERECTION AID

CROSS REFERENCE TO RELATED APPLICATION

This is a continuation-in-part of application Ser. No. 047,489 filed May 11, 1987 and now abandoned.

SPECIFICATION

This invention relates to an erection aid of the type in which an inflatable annulus surrounds the penis and applies pressure thereto.

BACKGROUND OF THE INVENTION

An erection aid of the general type to which the present invention relates is shown in German Patentschrift No. 427,488. The device shown therein involves an inflatable elastic ring which encompasses the penis and which, when inflated by means of the valve provided for this purpose, is intended to subject the penis to ring compression. The effect of this is to block the flow of venous returning blood while permitting continued arterial flow into the penis. The corpora cavernosa thus fill and the desired erection is achieved. An erection aid of this type can be used to treat impotence of any kind whether due to psychological or physiological causes.

An advantage of this familiar construction is that the erection aid is in the form of a soft, elastic tube so that any risk of injury is avoided. Neither the penis nor the partner can be injured. No kind of injury can result from the bumping of the soft elastic tube against the female genital region.

This known construction is made with a uniformly constructed annular tube. This tubular ring, in accordance with its purpose, is intended to expand to some extent inwardly in order to achieve the desired compression effect. Resistance is created from within by the penis, however, which opposes the inward expansion of the ring. Thus, the known tube is forced to expand predominantly to the side, that is, in the direction of the longitudinal axis of the penis which is essentially the same as the central axis of symmetry of the ring. The result, therefore, is a substantial increase in the dimension of the ring in the direction of the length of the penis. This is disadvantageous because it diminishes the available length of penis which is essential for success in accordance with the purpose and threatens the success itself if the corresponding physical constitution of the patient is also a factor, particularly in the case of obesity in conjunction with below average penis length.

It is known to use a tube having uniform wall thickness but this does not work well because the tube expands primarily outwardly, not inwardly. In order to overcome this difficulty, efforts to confine the ring have been tried such as shown in U.S. Pat. No. 3,820,533, Jones, in which the confining structure constitutes a hard outer shell containing a ring of uniform wall thickness. However, this does not work either. If the rigid ring is formed so that its inner diameter equals the outer diameter of the flaccid penis, then when the elastic ring is inflated to cause erection, the penis expands radially and is strangulated by the inelastic confining structure. This is a dramatic, painful and dangerous situation. On the other hand, if the rigid ring is made with an inner diameter significantly larger than the flaccid penis, then the expanding tube has free, unconfined areas to the side (axially) in which areas the tube can expand in an uncontrolled fashion, forming bubbles wherever a slight thinning of the tube wall occurs. A similar result is obtained with structures such as shown in U.S. Pat. No. 4,417,567, Trick.

SUMMARY OF THE INVENTION

Accordingly, an object of the present invention is to provide an erection aid of the type including a soft, elastic inflatable ring which has a non-uniform wall thickness to control blood flow out of the penis and which is formed so that it conforms to the outer diameter of the penis both initially and as the penis grows radially.

A further object of the present invention is to provide an erection aid of the type including an inflatable ring which is soft and elastic and which has minimum axial length and a construction which minimizes the increase in axial length as inflation occurs.

Briefly described, the erection aid in accordance with the invention includes an endless tube of soft and elastic material forming an annular ring having a central axis of symmetry dimensioned to surround a human penis and valve means in the tube to permit selective inflow and outflow of air to thereby selectively increase and decrease the pressure within the tube. The wall of the tube is formed with non-uniform thickness with the thickness of that portion of the tube wall facing inwardly toward the central axis of the annular tube being significantly thinner and more easily deformable than the outwardly facing wall portions. The wall thickness changes along generally circular transition lines each of which has a diameter substantially equal to the outer diameter of a flaccid penis so that as the pressure within the tube is increased the diameter of the inwardly facing surface of the tube decreases to apply pressure to the penis. The thicker portions of the ring are elastic so that the diameter of the transition lines can grow with the increasing diameter of the tumescing penis.

BRIEF DESCRIPTION OF THE DRAWING

In order to impart full understanding of the manner in which these and other objectives are attained in accordance with the invention, a particularly advantageous embodiment thereof will be described with reference to the accompanying drawings, which form a part of this specification, and wherein;

FIG. 2 is a sectional view along line 2—2 of FIG. 1;

FIG. 3 is a view similar to FIG. 2 but at a greater inflation pressure; and

DESCRIPTION OF THE PREFERRED EMBODIMENTS

Figure 1:
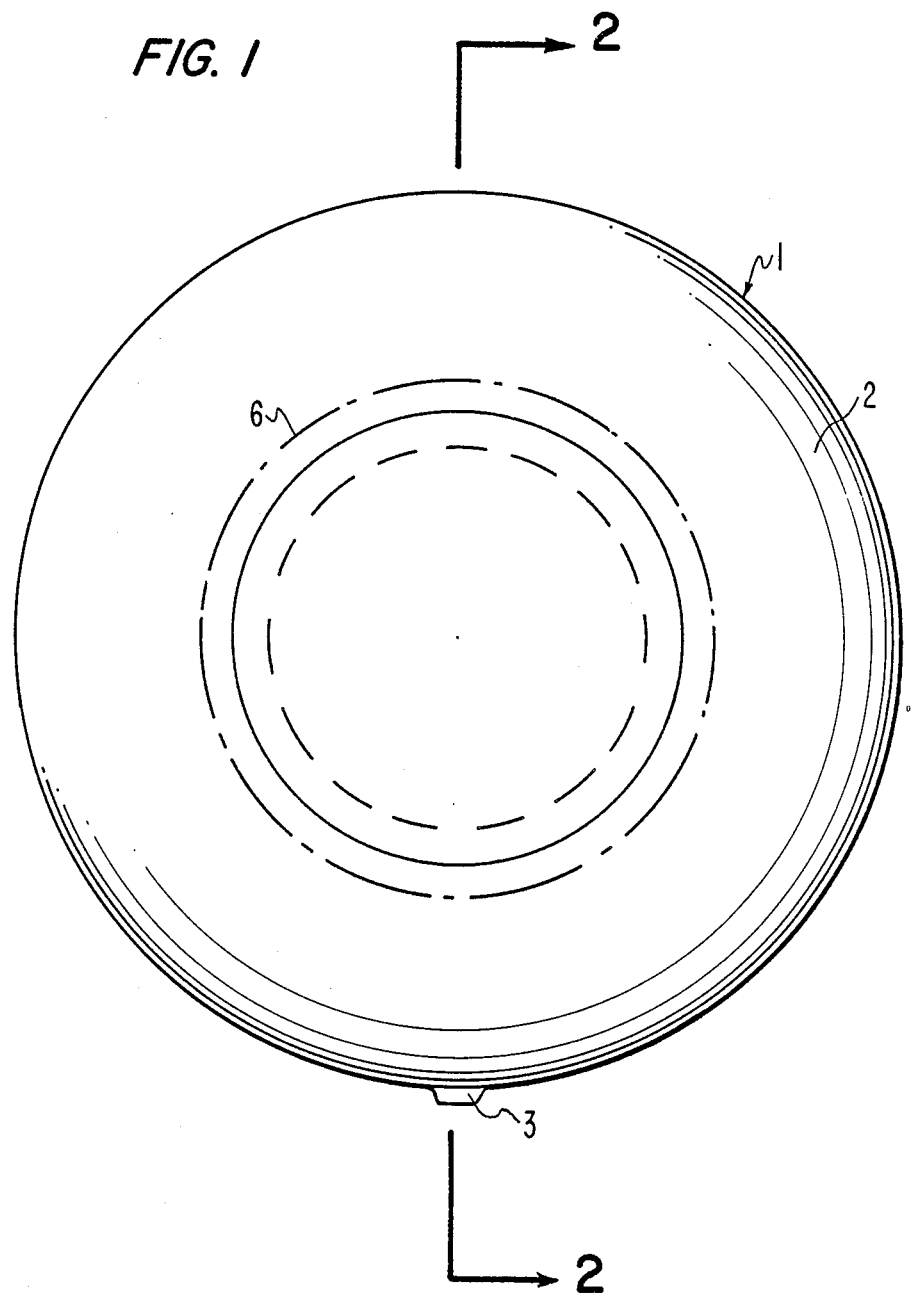
FIG. 1 is an enlarged side elevation of an annular inflatable tube in accordance with the present invention with very small inflation pressure.

As shown in FIG. 1, the erection aid indicated generally at 1 in accordance with the invention includes an annular, ring-shaped tube 2 which is seen in cross section in FIG. 2.

At an exterior point on the ring is provided a valve 3 which is shown only schematically in the drawings. Any of a variety of valve forms can be used, but the preferred valve is a conventional, commercially available valve which comprises a check or reflux valve which has the capability of being released to permit deflation. Thus, with a simple hand pump (such as a syringe) attachable to the outside of valve 3, the pressure within the tube 2 can be increased. Through appropriate valve manipulation, the elevated pressure can be reduced. In this way, the internal pressure within the tube 2 can be varied and established as desired.

As shown in FIGS. 1 and 2, the tube is only slightly inflated to the point at which it reaches a form having some stability which is required in order to handle and use it. In this basic form, it has a tube diameter or ring width B as shown in FIG. 2 of approximately 7-10 mm. The inside diameter D1 of the annular ring is approximately 25 mm in the basic design for standard penis dimensions. Smaller or larger sizes can, of course, be prepared to accommodate physiological variations.

At these dimensions, the inside diameter D1 of the annular ring is approximately equal to the normal flaccid penis diameter and can easily be pushed onto the organ. Pressure at this time is close to atmospheric pressure. As will be recognized, when the ring is even slightly inflated, the inside diameter is initially decreased, applying pressure on the penis in the desired manner.

If the tube consisted of material having a uniform wall thickness throughout, as in the known construction, then not only would the inside diameter D1 decrease upon inflation but the outside diameter would also grow and the width B can be expected to increase in an undesirable manner. Since the reduction of the inside diameter D1 is opposed by the counter pressure of the penis, the growth in width B, in particular, will be greater. During creation of the desired pressure, the width can be more than tripled under certain circumstances.

According to the invention, the outside part of tube 2, relative to the axis of symmetry 8 of the ring 1, is reinforced. As shown in FIG. 2, the wall thickness of the outer region 4 of the tube is considerably greater as compared with the wall thickness of the relatively thin inwardly facing region 5. The transition is gradual, as illustrated, which is advantageous in that no disruptive edges are created.

The preferred embodiment is represented in the Figures. As shown in FIG. 2, which comprises a section through the axis of symmetry of the ring with just enough pressure in the tube to give it shape so that it can be handled, it will be seen that approximately three-quarters of the circumference of the tube, in the sectional view, includes material having greater wall thickness. Thus, approximately one-quarter of the circumference of the tube, including that portion which is closest to the axis of symmetry of the ring and faces inwardly toward that axis, consists of material having thinner wall thickness.

While the difference in wall thickness depends to some extent on the elasticity characteristics of the material selected to manufacture the article, a device constructed using a type of rubber commonly employed in the manufacture of surgical tubing is satisfactory with a thickness ratio of approximately 4:1.

When the internal pressure within the device is increased beyond atmospheric pressure in the structure according to the invention, the thin-walled inner region 5 expands inwardly toward the central axis as illustrated in FIG. 3 and the desired reduction of the inside diameter to a measurement D2 is accomplished. This reduced inside diameter is also illustrated by a broken line in FIG. 1.

FIG. 2 shows the inflation setting with the larger inside diameter D1 in which the ring is applied to the flaccid penis. The inside diameter D1 is therefore intended to be essentially equivalent to the penis diameter. It can then be pushed onto the penis with slight force while the elastic part 5 is expanded. The advantage of this is that the reinforced region 4 with its edge 6 reaches directly to the penis so that sideways deformation of the ring is completely eliminated.

Figure 6:
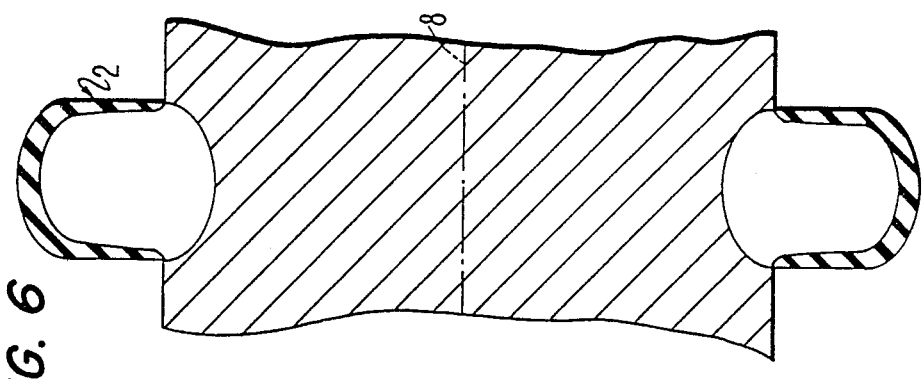
FIGS. 4, 5, and 6 are sectional views along the axis of the penis and the annular tube showing three different conditions of inflation and erection.
Figure 5:
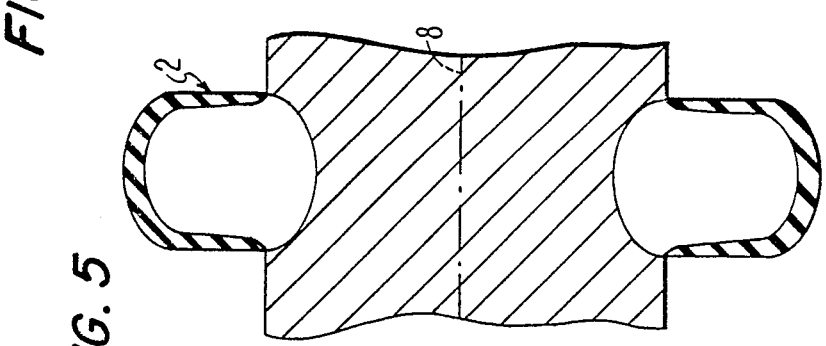
Figure 4:
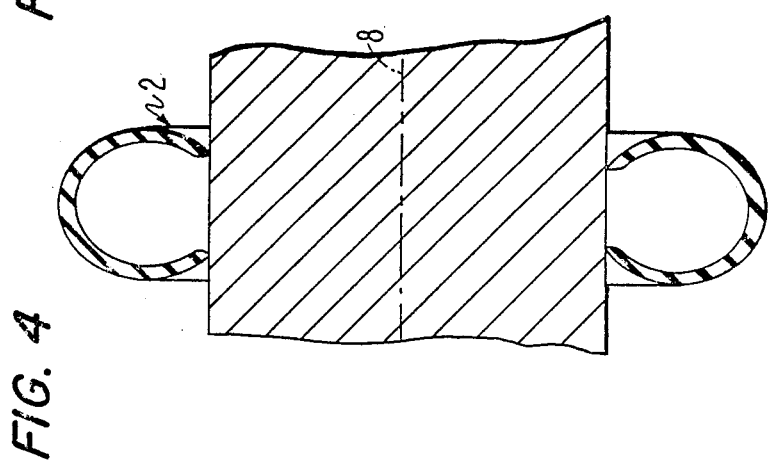

Referring now to FIGS. 4, 5, and 6, the manner in which the device functions and is used can be seen. In FIG. 4 the ring in the state of low inflation described in connection with FIG. 2 is placed at the root of the flaccid penis. The pressure in the ring is then increased so as to expand the thinner portion 5 radially inwardly, as shown in FIG. 5, applying pressure to the penis, At the root of the penis where the ring is placed, there are veins and arteries under the skin. When moderately low pressure is applied to those veins and arteries, the veins which are carrying blood under low pressure are compressed and, therefore, flow is blocked. The arteries, in which the pressure of pumping blood is always much higher, continue to carry blood into the penis. Thus, blood goes in but cannot leave, creating tumescence and the penis grows in diameter.

As shown in FIG. 6, the penis has become larger and more rigid than the flaccid state and the ring has also become larger although it continues to have essentially the same cross-sectional shape as in the condition of FIG. 5. Significantly, it has grown in diameter with the penis.

As seen in FIGS. 4 and 5, the ring as positioned on the flaccid penis is such that the edge or transition line between the thicker and thinner parts rests against the penis. Thus, the entire surface of the thinner part 5 is engaged by the penis. It is thus not possible for portions to expand or bubble in an uncontrolled manner. Nevertheless, the thicker part has sufficient elasticity so that it can enlarge and follow the growth of the penis from the condition shown in FIG. 5 to that of FIG. 6 so that no strangulation occurs.

Thus, it will be seen that the erection aid in accordance with the invention has an annular tube the outside of which has form stability and prevents expansion of the tube in the direction of the axis of symmetry of the ring, i.e., in width, during inflation of the tube. The ring can thus essentially be expanded inwardly in the desired direction and essentially retains its width during inflation. The usable free penis length is therefore not unnecessarily restricted but the ring is capable of enlarging with penis growth so that discomfort or harmful effects are avoided.

While one advantageous embodiment has been chosen to illustrate the invention, it will be understood by those skilled in the art that various changes and modifications can be made therein without departing from the scope of the invention as defined in the appended claims.

What is claimed is:

1. An erection aid comprising
   an endless tube of soft and elastic material forming an annular body having a central axis and dimensioned to surround the human penis, the outer diameter of said tube being substantially the same in both the axial and radial directions of the annular body; and valve means in said tube to permit selective inflow and outflow of air to thereby selectively increase and decrease the pressure within said tube, the wall of said tube being formed with nonuniform thickness, the thickness of that portion of the tube wall equal to about one-fourth of the circumference of said wall facing inwardly toward said central axis, as viewed in section along a plane containing said axis, being significantly thinner and more easily deformable than the remaining, thicker, outwardly facing wall portions, equal to about three-quarters of the circumference of said wall, the wall thickness changing along transition lines each having a diameter substantially equal to the outer diameter of a flaccid penis so that as the pressure within said tube is increased the diameter of the inwardly facing surface of said tube decreases substantially uniformly to apply pressure to the penis, said thicker portions being sufficiently elastic so that the diameter of said transition lines can increase with the growing diameter of the tumescing penis, thereby avoiding excessive constriction of the penis.

* * * * *